United States Patent
Masson (10) Patent No.: US 8,936,645 B1
(45) Date of Patent: Jan. 20, 2015

(54) SURGICAL PROCESS FOR RESURFACING A HUMERAL HEAD

(71) Applicant: Marcos V. Masson, Houston, TX (US)

(72) Inventor: Marcos V. Masson, Houston, TX (US)

(*) Notice: Subject to any disclaimer, the term of this patent is extended or adjusted under 35 U.S.C. 154(b) by 33 days.

(21) Appl. No.: 13/666,464

(22) Filed: Nov. 1, 2012

(51) Int. Cl.
*A61F 2/40* (2006.01)

(52) U.S. Cl.
CPC .................................... *A61F 2/4014* (2013.01)
USPC .................. 623/19.11; 623/19.12; 623/19.13; 623/19.14

(58) Field of Classification Search
CPC .................................... A61F 2/40; A61F 2/46
USPC ..................... 623/18.11–19.14, 23.11–23.19, 623/23.4–23.44; 606/86 R–91
See application file for complete search history.

(56) References Cited

U.S. PATENT DOCUMENTS

| | | | |
|---|---|---|---|
| 4,550,450 A | 11/1985 | Kinnett | |
| 7,585,327 B2 | 9/2009 | Winslow | |
| 8,152,855 B2 * | 4/2012 | Tulkis et al. | 623/23.12 |
| 2004/0034431 A1 | 2/2004 | Maroney et al. | |
| 2005/0043805 A1 | 2/2005 | Chudik | |
| 2006/0009852 A1 | 1/2006 | Winslow et al. | |
| 2007/0016304 A1 | 1/2007 | Chudik | |
| 2008/0021564 A1 | 1/2008 | Gunther | |
| 2010/0292802 A1 | 11/2010 | Borowsky | |
| 2011/0313533 A1 | 12/2011 | Gunther | |
| 2012/0296436 A1 * | 11/2012 | Klawitter et al. | 623/19.14 |

* cited by examiner

*Primary Examiner* — Yashita Sharma
(74) *Attorney, Agent, or Firm* — Egbert Law Offices, PLLC (57) ABSTRACT

A surgical process for resurfacing a head of a humerus has the steps of applying a jig over a surface of the head so as to define a separation line between the head and the humeral shaft, sawing along the separation line so as to separate the head and the humeral shaft so as to expose an end of the shaft, applying a resurface implant over an exterior surface of the head, and affixing the head having the resurface implant thereon onto the exposed end of the shaft. The head is shaped so as to smooth the exterior surface of the head prior to the step of applying the jig. A hole is formed through the head so as to extend into the shaft. A stem of the resurface implant extends through the hole in the head and into the hole in the shaft.

11 Claims, 5 Drawing Sheets

SURGICAL PROCESS FOR RESURFACING A HUMERAL HEAD

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to shoulder surgery. More particularly, the present invention the relates to surgical processes whereby the head of the humerus receives a resurface implant that thereon. Additionally, the present invention relates to surgical process whereby the head of the humerus is removed and reattached during the process of applying the resurface implant.

2. Description of Related Art Including Information Disclosed Under 37 CFR 1.97 and 37 CFR 1.98.

The shoulder joint, the largest joint in the upper extremity, functions as the fulcrum for all functional activities of the upper extremity, and also affords the greatest range of motion and planes of motion of any joint in the body. These unique characteristics of relatively high force transmission as well as the large range of motion afforded by the unique anatomical structure of this joint, impart certain difficult considerations in total shoulder prosthetic design. The design must allow for the shoulder to be the foundation joint for the upper extremity with its large range of motion as well as for the limited osseous framework available for fixation of the device. Additional considerations include the proximity of neural and vascular anatomic structures, the usual difficult surgical approach to the shoulder secondary to major muscular structures, and the relationship of the acromiom to the gleno-humeral articulation.

Much prior prosthetic replacement development has been directed at the hip and knee joints, the major weight bearing joints of the lower extremity. However, these joints have a much less complex and extensive range of motion and the anatomical considerations in these joints, especially the hip, are much less complicated than the shoulder. The surgical approach to the hip and the knee is generally considered less demanding than the surgical approaches to the shoulder joint.

Of the several surgical options available for the painful shoulder with limited or no motion, gleno-humeral replacement, commonly accepted as total joint replacement for the shoulder, has offered the best solution for problems of the entire shoulder joint to date. At present, there are two basic categories of prosthesis available. These include constrained prosthesis and essentially unconstrained prosthesis. The major problems with the constrained prosthesis occur as in all constrained prosthesis, i.e., limited motion, mechanical failure, and loosening. In the unconstrained category, the prosthesis usually available utilizes surface or flush glenoid components with fixation devices directed to the anatomical cancellous region of the scapulae. Fixation of the glenoid component has and continues to be considered a problem. Incomplete recovery of range of motion primarily in abduction and forward flexion has been encountered and appears to be related to overall prosthetic design. Another problem area in the present gleno-humeral replacement is proximal subluxation of the humerus with resulting humeral acromial impingement.

The conventional techniques of shoulder replacement surgery requires surgical transection of a rotator cuff to gain sufficient exposure of the joint surfaces of the shoulder. After the joint surfaces are replaced, the rotator cuff tendon must be surgically repaired with suture material. This tenuous repair necessitates an obligatory period of approximately six weeks for the rotator cuff tendon to heal before advanced shoulder rehabilitation can be performed. This surgical transection and subsequent repair, as well as the delay in rehabilitation, hold significant consequences for the functional outcome of the shoulder replacement including permanent weakness and decreased range of motion.

Additionally, despite the extensive exposure, conventional methods for shoulder replacement surgery still fail to properly restore the native anatomic relationships of the joint surfaces of the shoulder. Conventional methods prepare the humeral surfaces of the shoulder joint by referencing off the intramedullary axis of the humeral shaft. This poses great difficulty for the surgeon since the intramedullary axis has an inconsistent relationship to the humeral surface. The humeral joint surface also possesses a complex anatomy with significant variability which cannot be entirely restored with conventional methods and implants. There exists much variability in the humeral head neck-shaft angle, posterior and medial offset, version (rotation), height, thickness, and radius of curvature. The failure to restore the native anatomic relationships and biomechanics to the shoulder joint has proven to result in a significantly lesser functional and durable outcome Conventional methods of shoulder replacement surgery also have difficulty gaining access to the glenoid joint surface. The glenoid surface of the shoulder joint is best prepared by working along an axis perpendicular to its surface. Because the humeral head sits in the way, this is a nearly impossible task with conventional methods. The humeral head has to be partially removed, the subscapularis (anterior shoulder rotator cuff muscle) transected, and the proximal humerus dislocated to even get close to working along this axis. Because of this difficulty, a majority of orthopedic surgeons still choose not to replace the glenoid surface despite clinically proven results of improved pain relief and function for shoulder replacement surgery when both the humeral and glenoid surfaces are replaced.

In these prior processes for the resurfacing of the head of the humerus, various jigs are utilized so that the resurface implant is properly applied over the head of the humerus. Typically, these jigs will extend outward referencing off the intramedullary axis of the humeral shaft, so as to provide a surface extending over the head. It is known that there is a great deal of variation in human beings between the orientations between the humeral head and the humeral shaft. Additionally, many surgeons have a great deal of difficulty in attempting to properly align the jig so that the resurface implant is properly applied onto the humeric head. Since the quality of surgeons varies greatly, inexperienced or less capable surgeons will often have a great deal of difficulty in properly orienting the resurface implant with the humerus. Additionally, the variations in anatomical structures will also cause a great deal in variation in the ability to properly place the resurface implant onto the head of the humerus. As such, a need has developed so as to orient the resurface implant in relation to the head of the humerus rather than in relation to the intramedullary axis of the humeral shaft.

In the past, various patents have issued relating to surgical process and apparatus for the resurfacing of the humeral head. For example, an early patent is that of U.S. Pat. No. 4,550,450, issued on Nov. 5, 1985 to J. G. Kinnett, provides a total shoulder replacement arthroplasty system which encompasses replacement of the articular surface of the humerus and adjacent glenoid articular surface with a humeral component having a convex surface and a shallow trapezoidal fixation keel to avoid violation of the medullary cavity by the prosthesis and with a concave overmounted glenoid component having a similar keel. The inferior aspect of the acromion is resurfaced with an acromial component for replacement of the acromial clavicular joint so as to provide the mechanical advantage of a fulcrum for abduction and forward flexion of the humerus.

U.S. Pat. No. 7,585,327, issued on Sep. 8, 2009 to M. A. Winslow, provides a resurfacing implant having a head and an extended articulating surface protruding from a portion of the head. This resurfacing implant is operable to articulate with at least one of a bone and a ligament. The head has an exterior articulating surface, an interior surface opposite the exterior articulating surface, and an anchoring device extending from the interior surface.

U.S. Patent Publication No. 2010/0292802, published on Nov. 18, 2010 to K. Borowsky, provides a shoulder replacement prosthesis that has a head for replacing the humeral head and a connection shaft. The head has a domed portion and a flange positioned at an end region of the domed portion. The flange has a width which varies around the domed portion. The flange has a greater width at a part corresponding to a region of the greater tuberosity than at a part corresponding to a region of the lesser tuberosity. The flange is provided with a plurality of connection portions for securing the tendons attached to the tuberosities. By dimensioning the flange appropriately, the anatomical positioning of the tendon-to-bone connections can be more accurately replicated.

U.S. Patent Publication No. 2004/0034431, published on Feb. 19, 2004 to Maroney et al., discloses a modular prosthetic assembly for use during performance of a shoulder replacement procedure on a patient. The modular prosthetic assembly includes a stem component configured to be implanted into a medullary canal of a humerus of the patient. The assembly also includes a prosthetic head component configured to be secured to a proximal end portion of the stem component. The prosthetic head component has a glenoid-bearing portion which is configured to bear against a glenoid surface of a scapula of the patient when the stem component is implanted into the medullary canal of the humerus of the patient and the prosthetic head component is secured to the stem component. The prosthetic head component also includes an acromion-bearing portion which is configured to bear against an acromion of the patient during abduction of the humerus when the stem component is implanted into the medullary canal of the humerus and the prosthetic head component is secured to the stem component.

U.S. Patent Publication No. 2006/0009852, published on Jan. 12, 2006 to Winslow et al., provides a two-piece humeral component for use in joint arthroplasty which is adapted to be implanted into a joint and engaged by a socket component of the joint. The joint component includes a body having a first articulating surface and a second medial surface opposite the first articulating surface. The first articulating surface is adapted to be engaged by the socket and the second medial surface is adapted to be secured to mounting portion. The mounting portion has a first surface and a second medial surface. The first surface is adapted to be fixably engaged to the second mounting portion of the humeral component. The second medial surface is adapted to be secured to the humerus.

U.S. Patent Publication No. 2005/0043805, published on Feb. 24, 2005 to S. C. Chudik, teaches a method and devices for shoulder replacement surgery that spares the rotator cuff. The method utilizes two anterosuperior passages to gain access to the glenohumeral joint, neither of which requires transaction of the rotator cuff. In addition, a transhumeral portal created through the second anterosuperior passage for use as a working tunnel. U.S. Patent Publication No. 2007/0016304, published on Jan. 18, 2007 to S. C. Chudik, shows a similar process and apparatus shoulder replacement surgery.

U.S. Patent Publication No. 2008/0021564, published on Jan. 24, 2008 to S. B. Gunther, describes a monoblock (non-modular) humeral head resurfacing implant designed to replace a portion of the patient's humeral head. The implant is designed to be performed either as a hemiarthroplasty or as a component of a total shoulder replacement along with a standard glenoid or inset glenoid implant.

U.S. Patent Publication No. 2011/0313533, published on Dec. 22, 2011 to S. B. Gunther, shows a humeral head resurfacing implant that comprises a body having an exterior articulating surface having a substantially hemi-spherical or elliptical shape, and an interior surface opposite the exterior articulating surface. The exterior articulating surface is capable of articulating with a glenoid of a patient. The interior surface includes a solid anterior portion that comprises a planar support surface for supporting the implant against a humeral head of the patient. The solid anterior portion fills at least 20% of the internal volume of said body. A stem portion extends outwardly from a central point within the interior surface.

It is an object of the present invention to provide a surgical process for the resurfacing a humeral head which assures the proper placement of the resurface implant in accordance with the natural anatomical structure of the patient.

It is another object of the present invention to provide a surgical process for the resurfacing a humeral head that creates more working space for the surgeon for the purposes of resurfacing and repairing the glenoid.

It is another object of the present invention to provide a surgical process for the resurfacing a humeral head that avoids the use of complicated jigs that are oriented to intramedullary axis of the humeral shaft.

It is a further object of the present invention to provide a process for the resurfacing a humeral head that allows surgeons of varying levels of skill to properly install the resurface implant.

It is a further object of the present invention to provide a surgical process for the resurfacing of a humeral head which assures that the resurface implant is securely positioned over the humeral head and imbedded within the humerus.

These and other objects and advantages of the present invention will become apparent from a reading of the attached specification and appended claims.

BRIEF SUMMARY OF THE INVENTION

The present invention is a surgical process for resurfacing a humeral head comprising the steps of: (1) applying a jig over a surface of the head so as to define a separation line between the humeral head and the humeral shaft; (2) sawing along the separation line so as to separate the head from the humeral shaft so as to expose an end of the humeral shaft; (3) applying a resurface implant over an exterior surface of the head; and (4) affixing the head having the resurface implant thereon onto the exposed end of the humeral head.

In the surgical process of the present invention, a guide wire is affixed through the head and into the humeral shaft such that the guide wire extends outwardly of the head. In particular, a centralizer cup is applied over the exterior surface of the head such that the guide wire extends through the wire pathway within the centralizer cup and penetrates into the head and the humeral shaft.

The exterior surface of the head is shaped prior to the step of applying the jig so as to smooth the exterior surface of the head. In particularly, a shaper is extended along the guide wire such that the shaper is centralized relative to the head. The shaper is applied onto the exterior surface of the head so as to smooth the exterior surface of the head.

In the surgical process of the present invention, a hole is formed through the head so as to extend into the humeral shaft. The resurface implant has a stem extending outwardly therefrom. The stem extends through the hole in the head such that the end of the stem resides in the hole in the humeral shaft. The exterior surface of the head resides adjacent an interior surface of the resurface implant.

The hole is broached so as to form a cruciform-shaped hole in the head. The resurface implant will have a stem having a cruciform cross-section conforming to the cruciform-shaped hole.

During the surgical process of the present invention, a cap can be applied over the exposed end of the humeral shaft subsequent to the step of sawing and prior to the step of affixing. The cap is removed from the exposed end of the humeral shaft prior to the step of affixing the head.

The foregoing Summary of the Invention is intended to describe the preferred embodiment of the present invention. This section is not intended to be limiting, in any way, of the broad scope of the present invention. The scope of the present invention is only to be limited by the following claims and their legal equivalents.

DETAILED DESCRIPTION OF THE INVENTION

The present invention is a surgical process for the placement of a resurface implant onto the humeral head. In order to expose the humeral head, standard surgical processes can be employed so as to separate the humeral head from the glenoid. Depending on the surgeon's preference, either a deltopectoral or the superior approach can be utilized. The advantages of the deltopectoral approach include the preservation of the deltoid origin and insertion, utilization of an extensile exposure, and facilitation of the subscapularis lengthening. The superior approach may be preferred since it is offers retention of the subscapularis. The deltopectoral approach is the most typical approach for the procedure. The deltopectoral approach is used to provide exposure to the anterior aspect of the glenohumeral joint, the upper humeral shaft, and the humeral head. An appropriate incision is made from the clavicle over the coracoid toward the deltoid insertion.

Various retractors can be utilized so as to separate the humeral head from the glenoid. A joint capsule is released anteriorly and inferiorly as needed, primarily from the humerus. Preservation of some of the posterior capsule is maintained to facilitate centralization and prevent posterior subluxation. The release of the anterior, inferior, and posterior glenohumeral ligaments is vital in properly and concentrically centralizing the humeral head. At this point, the humeral head should rotate freely into maximum external rotation, slight abduction, and significant extensions. This allows the head to dislocate anteriorly for surgical procedures on the humeral head.

Figure 1:
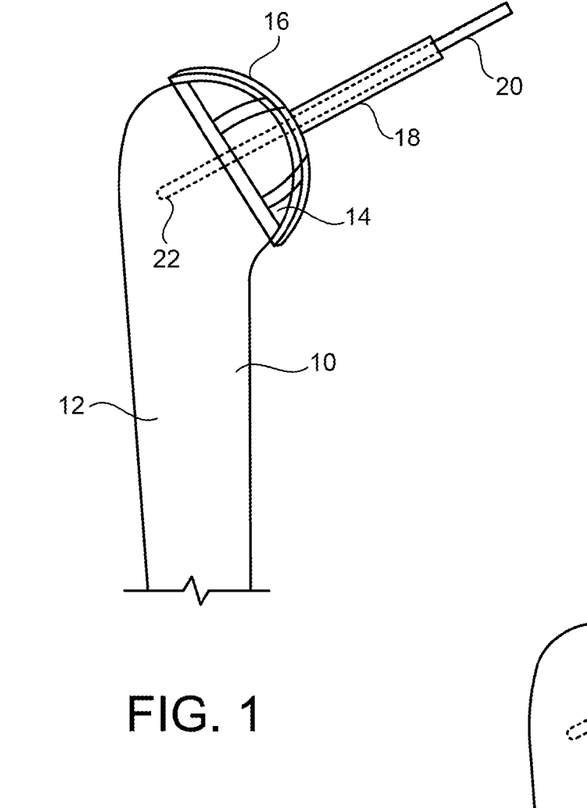
FIG. 1 is a side, partially transparent, view of the centralizer cup and guide wire as positioned onto the humeral head.

FIG. 1 is an illustration of the released humerus 10. The humerus 10 includes the humeral shaft 12 and the humeral head 14. A centralizer cup 16 is utilized on the humeral head 14. This centralizer cup 16 has a pair of functions. First, the centralizer cup 16 is able to locate the center of the anatomic humeral head. Secondly, the centralizer cup 16 determines the implant size that best fits the patient's anatomy. During the typical surgical procedures, a large variety of centralizer cups are made available to the surgeon. The surgeon can simply choose from the various sizes of centralizer cups so as to find the cup which most easily fits over the unshaped humeral head. A properly centralizer cup 16 is determined by choosing a cup that fits over a deformed humeral head 18 with or without removal of osteophytes and with little if any protrusion.

Figure 2:
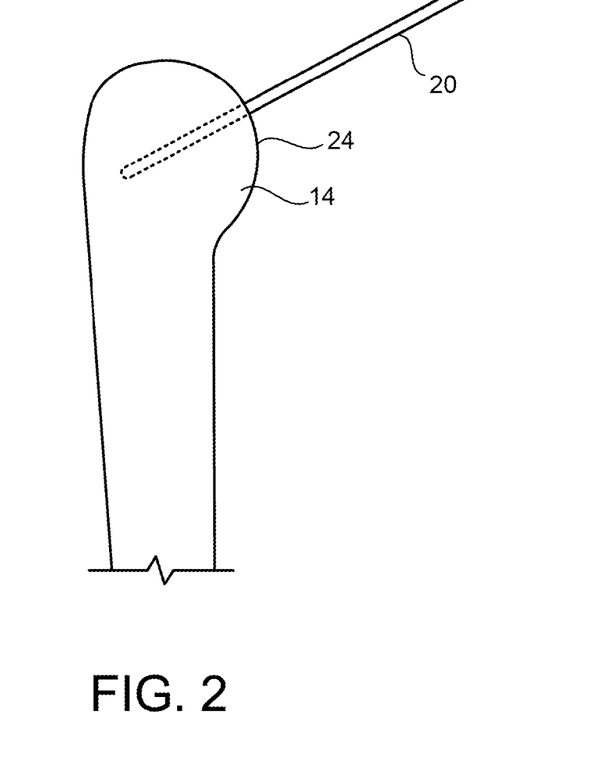
FIG. 2 is a subsequent step of the process of the present invention in which the guide wire extends outwardly of the humeral head.

The centralizer cup 16 has a tubular section 18 extending outwardly therefrom. The centralizer cup 16 is placed over the central axis of the articular surface in alignment with the properly neck-shaft angle (approximately 135°). A wire guide 20 is illustrated as extending through the tubular portion 18 of the centralizer cup 16. A wire driver can be utilized so as to place the wire guide 20 (otherwise known as a "Steinmann pin") through the cannulated tubular portion 18. The wire driver drives the end 22 of the wire guide 20 through the humeral head 14 and into the humeral shaft 12. As can be seen in FIG. 2, the centralizer cup 16 has been removed from the humeral head 14. As such, it can be seen that the wire guide 20 extends outwardly from the exterior surface 24 of the humeral head 14. As such, the wire guide 20 will provide the surgeon with guidance as to the proper central location for the application of the various procedures to be described hereinafter.

It should be noted that the centralizer cup 16 can be utilized so as to determine the size of the resurface implant. The outer dimensions of the centralizer cup 16 are the same as the resurface implant's outer dimension. The inside dimensions of the centralizer cup 16 are the same as the inside dimension of the resurface implant and the inside dimension of the shaper (to be described hereinafter). As a result, the interior of the centralizer cup 16 will indicate the amount of bone resection that should be performed by the shaper.

Figures 3, 4:
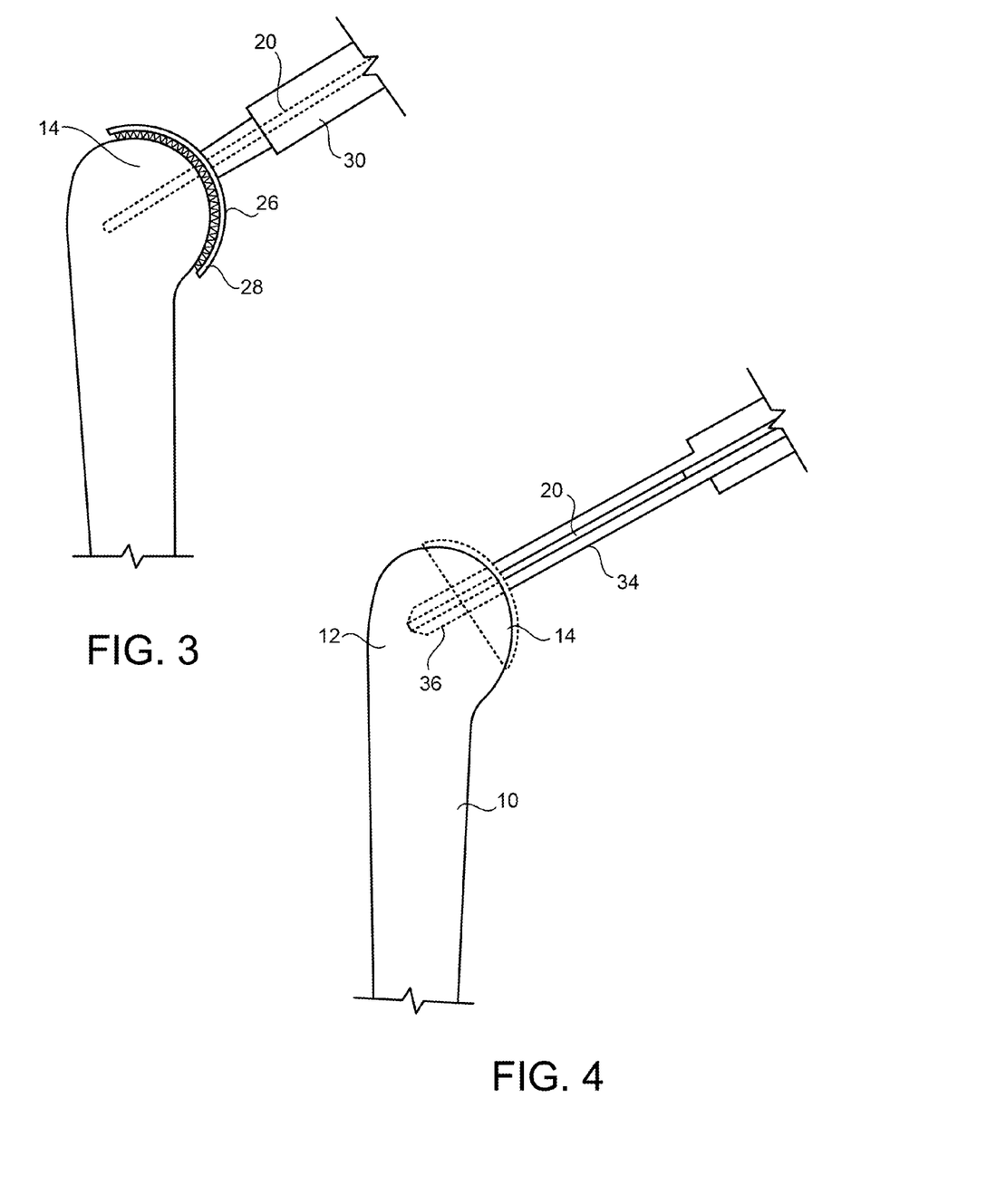
FIG. 3 shows the application of the shaper onto the guide wire so as to shape the surface of the humeral head.
FIG. 4 is a view of a subsequent step of the present invention in which a drill and/or broach is applied over the guide wire so as to form a hole through the head and into the humeral shaft.

FIG. 3 illustrates that a shaper 26 is applied to the exterior surface of the humeral head 14. The shaper 26 can be in the nature of a reamer which servers to smooth the exterior surface 24 of the humeral head 14. The shaper 26 will have a curved head 28 that will generally conform to the shape of the exterior surface of the humeral head 14. The shaper 26 has a handle 30 that receives the guide wire 20 therethrough. As a result, the shaper 26 will be properly aligned and centralized by the guide wire 20 with respect to humeral head 14.

The shaper 26 will abrasively contact the exterior surface 24 of the humeral head 14 and will create a small rim of bone on which the resurface implant can be placed with minimal protruding edges. The guide wire 20 will maintain alignment with the shaper 26 and will avoid any problems associated with the dropping of the arm or elbow of the surgeon during the shaping of the humeral head 14. The shaping will proceed until either bone removal is seen at the center of the shaper 26 or the peripheral articular surface near the anatomic neck is reached.

Referring to FIG. 4, it can be seen that a broach 34 is utilized so as to form a hole 36. Hole 36 extends through the humeral head 14 and into the area of the humeral shaft 13 of the humerus 10. The broach 34 also receives the guide wire 20 therein so that the broach 34 is properly aligned with and centralized with the humeral head 14. As will be described hereinafter, the broach 34 will have a unique shape so as to facilitate the placement of the resurface implant onto the humeral head 14. In particular, the broach 34 can have a cruciform cross-section so as to create a cruciform-shaped hole within the humeral head 14. Within the concept of the present invention, it is important that the hole 36 extends entirely through the humeral head 14 and partially into the humeral shaft 12. Depending on the particular surgical requirement, a hole can be drilled by a drill applied to the guide wire 20 initially. Subsequently, the broach can be utilized so as to form the specific shape of the hole. Ultimately, the shape of the hole 36 should generally conform with the shape of the stem of the resurface implant so as to secure the resurface implant against rotation.

If drilling is initially used, the broaching sequence will follow. The broach 34 is placed over the guide wire 20 and advanced into the pilot hole (created by drilling) with a mallet. It is important to maintain proper valgus-varus and version so as to ensure complete seating of the broach 34 against the humeral head 14. Additional broaches can be utilized so as to increase the broach size, as required.

Figure 5:
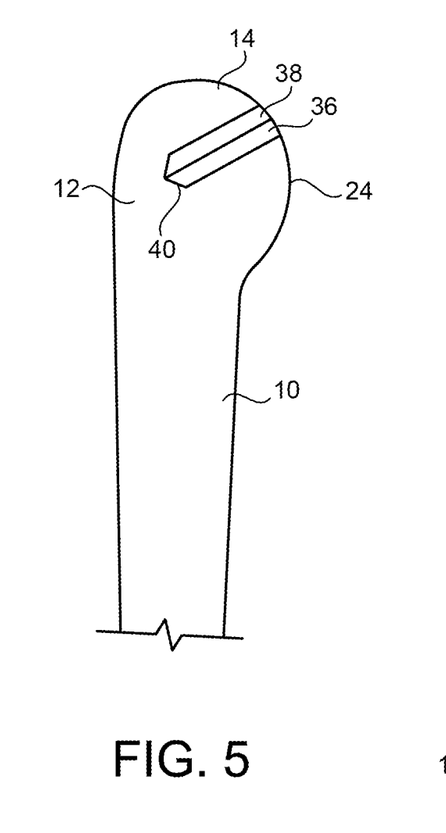
FIG. 5 is an illustration showing the hole that has been formed into the humeral head by the tool of FIG. 4.

FIG. 5 illustrates that the guide wire 20 and the broach 34 have been removed from the humeral head 14. As a result, the hole 36 remains. The hole 36 will have an end 38 that opens at the exterior surface 24 of the humeral head 14. The end 40 of the hole 36 will terminate within the humeral shaft 12 of the humerus 10.

Figure 6:
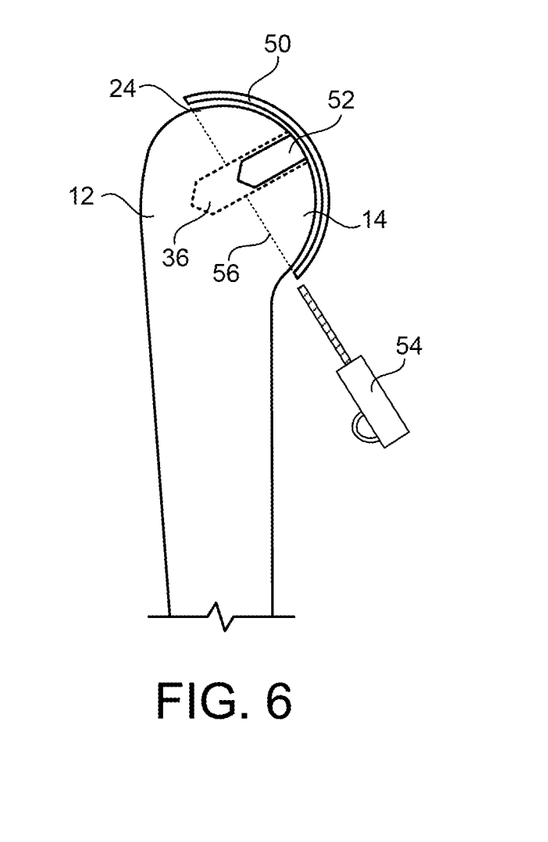
FIG. 6 illustrates that application of a saw onto the separation line between the humeral head and the humeral shaft so as to separate the head from the humeral shaft.
Figure 7:
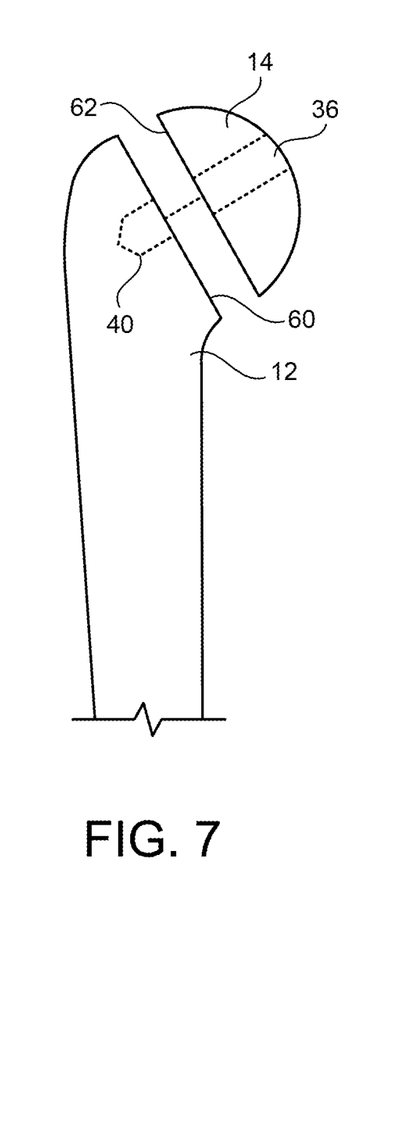
FIG. 7 is an illustration of the head as separated from the humeral shaft.

FIG. 6 illustrates the next step in the process of the present invention. As can be seen, a jig 50 is applied over the exterior surface 24 of the humeral head 14. The jig 50 will have a shape generally conforming to the exterior surface 24 of the humeral head 14. The jig 50 includes a stem 52 that can be inserted into the hole 36 so as to ensure that the jig 50 is properly centralized relative to the humeral head 14. A saw 54 (or other cutting instrument) is illustrated as being directed toward a separation line 56 defined by the edges of the jig 50. The surgeon can separate the humeral head 14 from the humeral shaft 12 by sawing along the separation line 56. Since the jig 50 will cover the humeral head 14, it is only necessary for the surgeon to follow a path adjacent to the edges of the jig 50 in order to properly cut along the separation line 56. The jig 50 can have a wide variety of configurations. As an alternative, the jig 50 can include a suitable slot wherein the saw 54 can be positioned within the slot so as to create the requisite cut.

Figure 9:
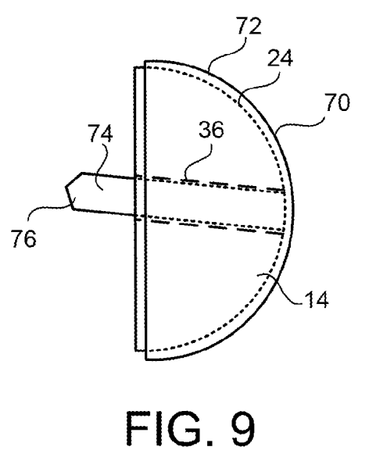
FIG. 9 is a side elevational view showing the resurface implant as applied over the exterior surface of the head.

FIG. 9 illustrates that the humeral head 14 has been separated from the humeral shaft 12 such that the humeral shaft 12 has an exposed end 60. The surface 62 of the humeral head 14 will be of a shape that properly mates with the exposed end 60. The hole 36 is illustrated in broken lines as extending entirely through the humeral head 14 and partially into the humeral shaft 12. The end 40 of the hole 36 will terminate inwardly of the exposed end 60 of the humeral shaft 12.

Figure 8:
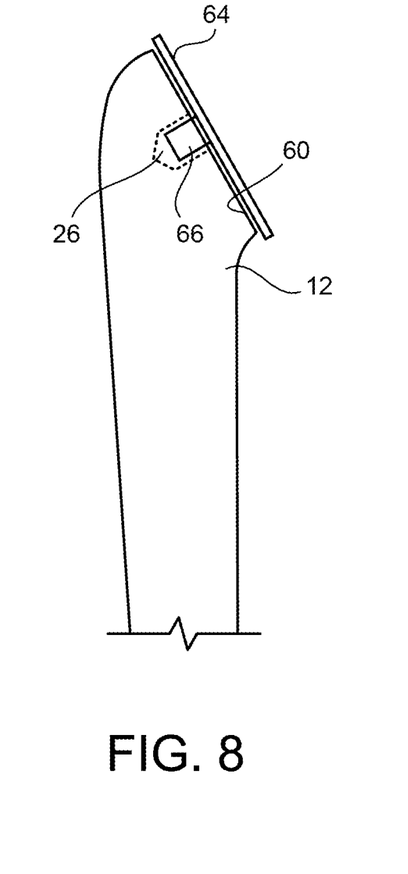
FIG. 8 is an illustration showing the application of a cap onto the exposed end of the humeral shaft.

Following the separation of the humeral head 14 from the humeral shaft 12, it is necessary to place a cap over the exposed end 60. FIG. 8 illustrated that the cap 64 is placed over the exposed end 60. The cap 64 can have a stem 66 that is received within the hole 36 in the humeral shaft 12.

Since the tissues at the exposed end 60 of the humeral shaft 12 are relatively soft, it is desirable to place the cap 64 over these surfaces. As such, any potential damage to the exposed end 60 can be avoided. The cap 64 can remain in place until such time when it is necessary to secure the humeral head 14 back onto the exposed end 60 of the humeral shaft 12.

FIG. 9 illustrates the application of the resurface implant 70 onto the separated humeral head 14. The resurface implant 70 has a smooth hemispherical surface 72 thereon. The outer surface 24 of the humeral head 14 will reside adjacent to the inner surface of the resurface implant 70. The resurface implant 70 has a stem 74 extending therefrom. It can be seen that the stem 74 will extend entirely through the hole 36 in the humeral head 14 so as to have an end 76 protruding outwardly of the resurface implant 70.

Figure 10:
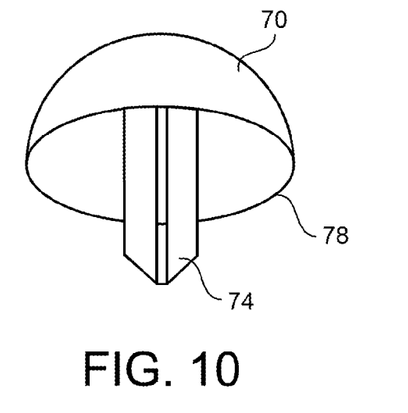
FIG. 10 is a perspective view showing the resurface implant in accordance with the present invention.

FIG. 10 shows the resurface implant 70 as having a generally hemispherical shape. The stem 74 has considerable length which extends outwardly beyond the end 78 of the hemispherical shape of the resurface implant 70. The stem 74 is illustrated as having a cruciform cross-section.

Figure 11:
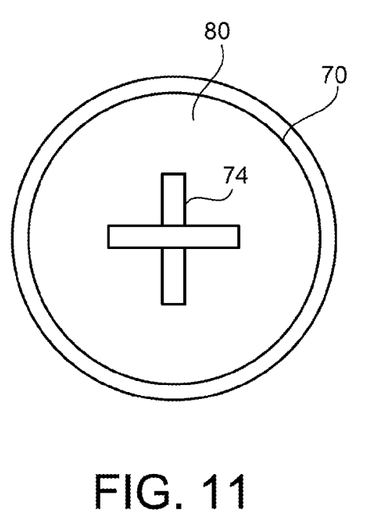
FIG. 11 is a bottom view showing the cruciform shape of the stem of the resurface implant of the present invention.

FIG. 11 illustrated the stem 74 as positioned centrally of the resurface implant 70. The stem 74 is positioned so as to extend from the inner surface 80 of the resurface implant 70. The stem 74 has a cruciform cross-section.

Within the concept of the present invention, it is important that the resurface implant 70 has a cruciform-shaped stem 74. As was stated earlier, the hole 36 that is formed in the humeral head 14 and the humeral shaft 12 will also have a cruciform shape. As such, when the stem 74 is placed through this cruciform-shaped hole, the cruciform cross-section of the stem 74 will be structurally retained within the hole. As such, undesired rotation of the resurface implant 70 is effectively avoided.

Figure 12:
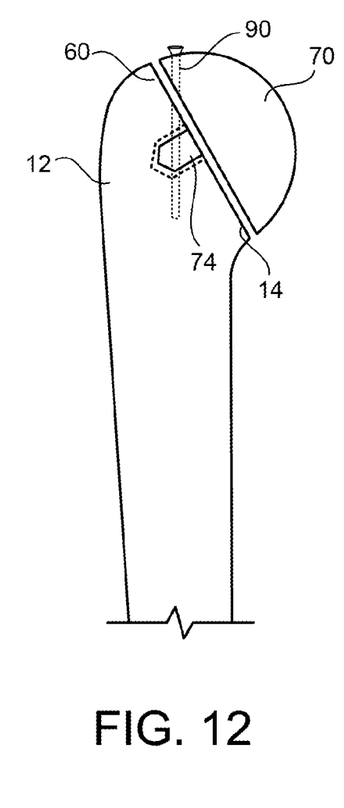
FIG. 12 is an illustration showing the resurface implant as positioned onto the exposed end of the humeral shaft.

FIG. 12 illustrated the affixing of the humeral head 14 back onto the exposed end 60 of the humeral shaft 12. The stem 74 extends within the hole that has been formed inwardly of the exposed surface 70 of the humeral shaft 12. As such, the resurface implant 70 will remain in position. Since the boney surface of the humeral head is positioned in surface-to-surface contact with the exposed end 60 of the humeral shaft 12, natural bone growth therebetween will be easily accomplished. As such, after a short amount of healing time, the humeral head 14 will be integrally joined with the humeral shaft 12 in a natural anatomic manner. If necessary, a pin, screw or wire 90 can be affixed through the humeral head 14 and through the stem 74 so as to further secure the humeral head 14 to the humeral shaft 12. This further assures a secure connection between the humeral head 14 and the humeral shaft 12.

Within the concept of the present invention, the stem 74 can be formed of a osteoconductive or osteoinductive material. As such, natural bone growth will cross link with the osteoconductive or osteoinductive material of the stem 74 so as to further secure the resurface implant 70 in position.

The present invention achieves significant advantages over the prior surgical procedures in this field. Foremost, the centering of the resurface implant 70 is accomplished purely by reference to the humeral head. There is a no need for complicated jigs or other arrangements which tend to orient and centralized the resurface implant 70 with respect to the intramedullary canal of the humeral shaft 12. It is not necessary from the surgeons to use guesswork to properly orient the resurface implant. Once the guide wire is established, centralization of the other components is assured. As such, the ultimate anatomical structure of the resurface implant 70, along with the other components, accurately reflects the native anatomical structure of the patient.

The removal of the humeral head during the shoulder surgery opens up a great deal of space for the surgeon. In past procedures, the humeral head 14 greatly interferes with the ability of the surgeon to properly access the glenoid, and other shoulder structures. Once the humeral head has been removed, the surgeon can have complete and full access to the glenoid for the purposes of resurfacing the glenoid or for the application of other prosthetic structures into the glenoid area.

The foregoing disclosure and description of the invention is illustrative and explanatory thereof. Various changes in the steps of the described process can be made within the scope of the appended claims without departing from the true spirit of the invention. The present invention should only be limited by the following claims and their legal equivalents.

I claim:

1. A surgical process for resurfacing a humeral head, the surgical process comprising:
    applying a jig over a surface of the humeral head so as to define a separation line between the humeral head and a humeral shaft;
    sawing along said separation line so as to separate the humeral head and the humeral shaft so as to expose an end of the humeral shaft;
    applying a cap over the exposed end of the humeral shaft;
    applying a resurface implant over an exterior surface of the humeral head; and
    affixing the humeral head having the resurface implant thereon onto the exposed end of the humeral shaft.

2. The surgical process of claim 1, further comprising:
    affixing a guide wire through the humeral head and into the humeral shaft such that said guide wire extends outwardly of the humeral head.

3. The surgical process of claim 2, the step of affixing the guide wire comprising:
    applying a centralizer cup over the exterior surface of the humeral head, said centralizer cup having a wire pathway therein; and
    extending the guide wire through the wire pathway such that the wire penetrates through the humeral head and into the humeral shaft.

4. The surgical process of claim 2, further comprising:
    shaping the exterior surface of the humeral head prior to the step of applying the jig so as to smooth the exterior surface of the humeral head.

5. The surgical process of claim 2, further comprising:
    extending a shaper along the guide wire such that said shaper is centralized relative to the humeral head; and
    applying the shaper onto the exterior surface of the humeral head so as to smooth the exterior surface of the humeral head.

6. The surgical process of claim 1, further comprising:
    forming a hole through the humeral head so as to extend into the humeral shaft.

7. The surgical process of claim 6, said resurface implant having a stem extending therefrom, the step of affixing the humeral head comprising:
    extending said stem through said hole in the humeral head such that the end of said stem resides in the hole in the humeral shaft.

8. The surgical process of claim 6, said resurface implant having a stem extending therefrom, the step of applying the resurface implant comprising:
    extending said stem of said resurface implant through the hole in said humeral head so that an end of said stem extends outwardly of said hole in said humeral head, the exterior surface of the humeral head residing adjacent an interior surface of said resurface implant.

9. The surgical process of claim 6, further comprising:
    broaching said hole so as to form a cruciform-shaped hole in said humeral head.

10. The surgical process of claim 9, said resurface implant having a stem extending therefrom, said stem having a cruciform cross-section conforming to the cruciform-shaped hole.

11. The surgical process of claim 1, further comprising:
    removing said cap from the exposed end of the humeral shaft prior to the step of affixing the humeral head.

* * * * *